(12) United States Patent
Murai et al.

(10) Patent No.: US 8,148,585 B2
(45) Date of Patent: Apr. 3, 2012

(54) FLUOROOLEFIN IODIDE MIXTURE AND METHOD FOR PRODUCING THE SAME

(75) Inventors: Daisuke Murai, Ibaraki (JP); Mitsuru Maeda, Ibaraki (JP); Seiichiro Murata, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 13/119,775

(22) PCT Filed: Aug. 17, 2009

(86) PCT No.: PCT/JP2009/064381
§ 371 (c)(1),
(2), (4) Date: Mar. 18, 2011

(87) PCT Pub. No.: WO2010/032575
PCT Pub. Date: Mar. 25, 2010

(65) Prior Publication Data
US 2011/0207904 A1    Aug. 25, 2011

(30) Foreign Application Priority Data
Sep. 18, 2008  (JP) .................................. 2008-239232

(51) Int. Cl.
C07C 21/18    (2006.01)
C07C 17/25    (2006.01)

(52) U.S. Cl. ........................................ 570/136; 570/155

(58) Field of Classification Search .................. None
See application file for complete search history.

(56) References Cited

FOREIGN PATENT DOCUMENTS

| | | | |
|---|---|---|---|
| JP | 62-012734 | | 1/1987 |
| JP | 62012734 | * | 1/1987 |
| JP | 01-180837 | | 7/1989 |
| JP | 2003-246757 | | 9/2003 |
| WO | WO 2005/090270 A1 | | 9/2005 |
| WO | WO 2007/074632 A1 | | 7/2007 |

OTHER PUBLICATIONS

International Search Report from corresponding PCT application No. PCT/JP2009/064381 dated Nov. 17, 2009, 2 pgs.
International Preliminary Report on Patentability and Written Opinion from corresponding PCT application No. PCT/JP2009/064381 dated Apr. 28, 2011, 5 pgs.

* cited by examiner

*Primary Examiner* — Karl J Puttlitz
(74) *Attorney, Agent, or Firm* — Brinks Hofer Gilson & Lione

(57) ABSTRACT

Disclosed is a mixture of fluoroolefin iodides represented by the general formulae: $C_nF_{2n+1}CF_2CH\!=\!CF(CF_2CF_2)_mI$ [Ia] and $C_nF_{2n+1}CF\!=\!CHCF_2(CF_2CF_2)_mI$ [Ib] wherein n is an integer of 0 to 5, and m is an integer of 1 to 3. The fluoroolefin iodide mixture is produced by subjecting a fluoroalkyl iodide represented by the general formula: $C_nF_{2n+1}CF_2CH_2CF_2(CF_2CF_2)_mI$ [II] wherein n is an integer of 0 to 5, and m is an integer of 1 to 3, to an HF-elimination reaction in the presence of a basic compound.

6 Claims, No Drawings

FLUOROOLEFIN IODIDE MIXTURE AND METHOD FOR PRODUCING THE SAME

RELATED APPLICATION

This application is a 35 U.S.C. §371 national phase filing of International Patent Application No. PCT/JP2009/064381, filed Aug. 17, 2009, through which and to which priority is claimed under 35 U.S.C. §119 to Japanese Patent Application No. 2008-239232, filed Sep. 18, 2008.

TECHNICAL FIELD

The present invention relates to a fluoroolefin iodide mixture and a method for producing the same. More particularly, the present invention relates to a fluoroolefin iodide mixture that is effectively used as, for example, a comonomer for the production of fluorine-containing copolymer elastomers having an iodine group as a crosslinkable group, and a method for producing the same.

BACKGROUND ART

Monomer compounds in which the carbon atoms forming a double bond are directly bonded to iodine atoms are known; however, there are few examples of monomer compounds in which an iodine atom is bonded to the end of the long side chain. The synthesis of such monomer compounds using a known method has a long synthesis route and results in a poor yield; thus, productivity is extremely low (see Patent Documents 1 and 2).

Moreover, the synthesis of terminally iodized fluorine-containing monomers generally requires multistep reactions, each reaction of which is very troublesome. On the other hand, many unsaturated compounds having a bromine atom at the end of the long side chain are known; however, terminal bromine atoms have less reactivity than terminal iodine atoms.

PRIOR ART DOCUMENT

Patent Document

Patent Document 1: WO 2005/090270
Patent Document 2: JP-A-62-12734

OUTLINE OF THE INVENTION

Problem to be Solved by the Invention

An object of the present invention is to provide a fluoroolefin iodide mixture, which is an unsaturated compound in which an iodine atom is bonded to the end of the long side chain, requires a short synthesis route and results in an excellent yield; and a method for producing the same.

Means for Solving the Problem

The present invention provides a mixture of fluoroolefin iodides represented by the general formulae:

$$C_nF_{2n+1}CF_2CH=CF(CF_2CF_2)_mI \quad [Ia]$$

and $$C_nF_{2n+1}CF=CHCF_2(CF_2CF_2)_mI \quad [Ib],$$

wherein n is an integer of 0 to 5, and m is an integer of 1 to 3.
The mixture of fluoroolefin iodide is produced by subjecting a fluoroalkyl iodide represented by the general formula:

$$C_nF_{2n+1}CF_2CH_2CF_2(CF_2CF_2)_mI \quad [II],$$

wherein n is an integer of 0 to 5, and m is an integer of 1 to 3, to an HF-elimination reaction in the presence of a basic compound.

Effect of the Invention

The mixture of fluoroolefin iodides [Ia] and [Ib] of the present invention can be easily produced only by subjecting the fluoroalkyl iodide [II] to an HF-elimination reaction in the presence of a basic compound. The obtained fluoroolefin iodide mixture, in which both fluoroolefin iodides have a double bond and a terminal iodine group in their structures, is not only used as a comonomer for the production of fluorine-containing copolymers having an iodine group as a crosslinkable group, but also effectively used as an intermediate raw material for the synthesis of various compounds using these reactive groups.

EMBODIMENTS FOR CARRYING OUT THE INVENTION

The fluoroolefin iodide mixture of the present invention is produced as a mixture of products [Ia] and [Ib] by subjecting the —CF2CH2CF2— bond of a fluoroalkyl iodide represented by the general formula:

$$C_nF_{2n+1}CH_2CF_2(CF_2CF_2)_mI \quad [II]$$

n: 0 to 5
m: 1 to 3 to an HF-elimination reaction in the presence of a basic compound.

Here, the mixture of compounds [Ia] and [Ib] is formed because in the HF-elimination reaction of the fluoroalkyl iodide, the abstraction of the H atom of the methylene chain $CH_2$ and the F atom of either one of the fluoromethylene chains $CF_2$ linking back and forth to the H atom occurs equally in the antero-posterior position. Moreover, since the HF-elimination reactions of the produced fluoroolefin iodides equally occur, the proportion of the produced products [Ia] and [Ib] is approximately half and half. Although the products [Ia] and [Ib] cannot be separately identified because they are very similar structural isomers, a mixture of these compounds can be directly used as a synthetic starting material in combination with other substances because they have equivalent reactivity.

The fluoroalkyl iodides, which is used as a starting material, can be obtained by sequential addition reaction of perfluoroalkyl iodide of the general formula: $C_nF_{2n+1}CF_2I$ (n: 0 to 5) with vinylidene fluoride and then with tetrafluoroethylene. The terminal group of $C_nF_{2n+1}$ may have a non-linear structure, as in $(CF_3)_2CF$-group.

Examples of compounds obtained by addition reaction of perfluoroalkyl iodide with vinylidene fluoride include compounds of the following formulae:

$CF_3(CH_2CF_2)I$ $CF_3(CF_2)(CH_2CF_2)I$ $CF_3(CF_2)_2(CH_2CF_2)I$ $CF_3(CF_2)_3(CH_2CF_2)I$ $CF_3(CF_2)_4(CH_2CF_2)I$ $CF_3(CF_2)_5(CH_2CF_2)I$ $(CF_3)_2CFCF_2(CH_2CF_2)I$ $(CF_3)_2CFCF_2CF_2(CH_2CF_2)I$ $(CF_3)_2CFCF_2CF_2CF_2(CH_2CF_2)I$

The addition reaction of vinylidene fluoride is carried out in such a manner that the perfluoroalkyl iodide is subjected to an addition reaction with pressurized vinylidene fluoride in the presence of a peroxide initiator The number of addition is 1 or more, and preferably 1, although depending on the reaction conditions. In the present invention, the number of addition of vinylidene fluoride is 1. Although the reaction temperature depends on the degradation temperature of the initiator used, the reaction is generally conducted at about 80 to 120° C.; when a peroxide initiator that decomposes at a low temperature is used, the reaction can be conducted at 80° C. or below. As a peroxide initiator, tert-butyl peroxide, di(tert-butylcyclohexyl)peroxy-decarbonate dicarbonate, dicetylperoxydicarbonate, or the like may be used at a ratio of about 1 to 5 mol % with respect to the perfluoroalkyl iodide.

Subsequently, the vinylidene fluoride adduct of perfluoroalkyl iodide is subjected to an addition reaction with tetrafluoroethylene. Examples of resulting products include compounds of the following formulae:

$CF_3(CH_2CF_2)(CF_2CF_2)I$ $CF_3(CH_2CF_2)(CF_2CF_2)_2I$ $CF_3(CH_2CF_2)(CF_2CF_2)_3I$ $CF_3(CF_2)(CH_2CF_2)(CF_2CF_2)I$ $CF_3(CF_2)(CH_2CF_2)(CF_2CF_2)_2I$ $CF_3(CF_2)(CH_2CF_2)(CF_2CF_2)_3I$ $CF_3(CF_2)_2(CH_2CF_2)(CF_2CF_2)I$ $CF_3(CF_2)_2(CH_2CF_2)(CF_2CF_2)_2I$ $CF_3(CF_2)_2(CH_2CF_2)(CF_2CF_2)_3I$ $CF_3(CF_2)_3(CH_2CF_2)(CF_2CF_2)I$ $CF_3(CF_2)_3(CH_2CF_2)(CF_2CF_2)_2I$ $CF_3(CF_2)_3(CH_2CF_2)(CF_2CF_2)_3I$ $CF_3(CF_2)_4(CH_2CF_2)(CF_2CF_2)I$ $CF_3(CF_2)_4(CH_2CF_2)(CF_2CF_2)_2I$ $CF_3(CF_2)_4(CH_2CF_2)(CF_2CF_2)_3I$ $CF_3(CF_2)_5(CH_2CF_2)(CF_2CF_2)I$ $CF_3(CF_2)_5(CH_2CF_2)(CF_2CF_2)_2I$ $CF_3(CF_2)_5(CH_2CF_2)(CF_2CF_2)_3I$

In addition to these compounds, similar $(CF_2CF_2)_{1-3}I$ adducts can be used as those in which the terminal group of $C_nF_{2n+1}$ is $(CF_3)_2CF-$.

The addition reaction of the vinylidene fluoride adduct of perfluoroalkyl iodide with tetrafluoroethylene is carried out under the same conditions as in the vinylidene fluoride addition reaction. The number of addition is 1 or more, and preferably 1 to 3, although depending on the reaction conditions.

The thus-obtained fluoroalkyl iodide [II] is reacted with a basic compound to result in an HF-elimination reaction between the $CH_2$ group on the prefluoroalkyl group side and either of the $CF_2$ groups adjacent thereto, thereby producing a mixture of fluoroolefin iodides [Ia] and [Ib].

Examples of basic compounds include hydroxides of monovalent or divalent metal, such as lithium hydroxide, sodium hydroxide, potassium hydroxide, magnesium hydroxide, calcium hydroxide, and cesium hydroxide; carbonates of monovalent or divalent metal, such as sodium carbonate, sodium hydrogen carbonate, potassium carbonate, and potassium hydrogen carbonate; and inorganic basic compounds that are alkoxides of monovalent metal, such as sodium methoxide, sodium ethoxide, and potassium methoxide. Such a basic compound is used in a molar ratio of about 1 to 2, preferably about 1 to 1.5, and more preferably 1.05 to 1.2, with respect to the fluoroalkyl iodide [II].

Although the HF-elimination reaction can be carried out in the absence of a solvent, the reaction is preferably carried out in the presence of water or an organic solvent in terms of reaction efficiency and control of heat generation. Examples of organic solvents include alcohols, such as methanol, ethanol, propanol, and isopropanol; ethers, such as diethyl ether, 1,4-dioxane, and tetrahydrofuran; ketones, such as acetone, methyl ethyl ketone, and methyl isobutyl ketone; hydrocarbons, such as toluene and cyclohexane; aprotic polar solvents, such as acetonitrile, N,N-dimethyl formamide, N,N-diethyl formamide, N,N-dimethyl acetamide, N,N-diethyl acetamide, and N-methyl-2-pyrrolidone; and fluorine-containing organic solvents, such as hydrochlorofluorocarbon (e.g., HCFC-225) and hydrofluoroether (e.g., Novec HFE; a product of 3M). Preferably, alcohols are used. It is more preferable that such basic compounds or organic solvent solutions thereof are compatible with fluoroalkyl iodide.

It is preferable that alcohols or alcohol solutions in which a basic compound is dissolved, which are used as reaction solvents, are completely dehydrated, for example, by a method using a molecular sieve (e.g., molecular sieve 3A) before use. Thereby, the yield can be further improved.

Water or an organic solvent is used in a volume ratio of about 0.1 to 100, preferably about 1 to 10, and more preferably 3 to 6, with respect to the fluoroalkyl iodide [II]. However, a larger amount of solvent has no influence on the reaction efficiency; thus, the solvent is preferably used in a volume ratio of 3 to 6. Moreover, when the reaction is conducted in an aqueous solvent system, phase transfer catalysts, such as alkyl ammonium salts, alkyl phosphonium salts, and crown ethers, may be used in combination with the basic compound catalyst.

The HF-elimination reaction is carried out at about −50 to 30° C., preferably about −40 to 10° C., and more preferably about −30 to 5° C. Side reactions proceed at temperatures higher than this range, generating a large amount of by-product with an unknown structure. The reaction may be carried out at reduced pressure, atmospheric pressure, or increased pressure; in terms of ease of handling the reaction apparatus, the reaction is preferably carried out at atmospheric pressure. The reaction time is about 1 to 5 hours, and preferably about 2 to 3 hours, and the reaction is completed almost quantitatively.

When static phase separation is performed after the reaction is completed, the organic layer is separated and washed with water, for example, to remove the basic compound, and purification is then performed by distillation etc., according to a standard method, thereby obtaining the target fluoroolefin iodide mixture. When static phase separation is not occurred by using a polar solvent, for example, the solvent is distilled off under reduced pressure, followed by the same treatment as in the case where static phase separation is carried out.

EXAMPLES

The following describes the present invention with reference to examples.

Example 1

A compound of the formula: $CF_3(CF_2)_3CH_2CF_2CF_2I$ (99.8GC %) (100 g; 0.2 mol) was charged in a sealed 500-ml reactor equipped with a stirrer, and the reactor was cooled to an internal temperature of −20° C. A potassium hydroxide-ethanol solution containing 55.1 g (0.23 mol) of potassium hydroxide and 150 g of ethanol was completely dehydrated using a molecular sieve 3A, and slowly added dropwise while stirring so that the temperature in the reactor did not exceed −18° C. After completion of the addition, the temperature in the reactor was maintained at −20 to −18° C., and the reaction was terminated after 3 hours.

Cold water (0 to 5° C.) was added to the obtained product, and the mixture was stirred. After allowing to stand, the separated fluoroolefin iodide mixture layer (lower layer) was separated, and washed again with cold water (0 to 5° C.). Thus, 70.5 g (yield: 97%) of a fluoroolefin iodide mixture in the lower layer was collected. The gas chromatography analysis results were as follows:

| | |
|---|---|
| $CF_3(CF_2)_3CH=CFCF_2CF_2I$ | (46.6 GC %) |
| $CF_3(CF_2)_2CF=CHCF_2CF_2CF_2I$ | (53.2 GC %) |
| Unknown | (0.2 GC %) |

The reaction product was distilled off under reduced pressure at an internal pressure of 400 to 500 Pa, an internal temperature of 70 to 75° C., and an overhead top temperature of 55 to 57° C., thereby obtaining 68.1 g (distillation yield: 95%) of a purified reaction product (99.7GC %). From the results of $^1$H-NMR and $^{19}$F-NMR, the purified reaction product was identified as a mixture of the compounds represented by the above-described formulae.

$^1$H-NMR (CDCl$_3$, TMS): 6.6 to 6.9 ppm

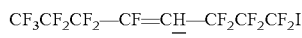

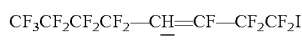

$^{19}$F-NMR (CDCl$_3$, C$_6$F$_6$): C$\underline{F_3}$C$\underline{F_2}$C$\underline{F_2}$—CF=CH—C$\underline{F_2}$C$\underline{F_2}$C$\underline{F_2}$I

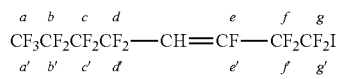

a,a': −82.1 ppm
b,b': −126.2 ppm
c: −119.7 ppm
c': −121.5 ppm
d: −109.0 ppm
d',e: −108.3 ppm
e': −110.7 ppm
f: −118.3 ppm
f': −117.4 ppm
g,g': −59.2 ppm

Example 2

When a potassium hydroxide-ethanol solution that was not dehydrated was used in Example 1, 65.1 g (yield: 81%) of fluoroolefin iodides were collected. The gas chromatography analysis results were as follows:

| | |
|---|---|
| $CF_3(CF_2)_3CH=CFCF_2CF_2I$ | (42.0 GC %) |
| $CF_3(CF_2)_2CF=CHCF_2CF_2CF_2I$ | (48.1 GC %) |
| Unknown | (9.9 GC %) |

Reference Example

A stainless steel reactor equipped with a stirrer was vacuumized, and the following components were charged therein:

| | |
|---|---|
| Water | 13 kg |
| $C_7F_{15}COONH_4$ | 39 g |
| $Na_2HPO_4 \cdot 12H_2O$ | 26 g |
| $CBr_2=CHF$ | 26 g |
| $ICF_2CF_2Br$ | 24 g |
| $C_4F_9CH=CF(CF_2)_2I$—$C_3F_7CF=CH(CF_2)_3I$ mixture (mixed molar ratio: 45/55) | 60 g |

Thereafter, 490 g (4.9 mol) of tetrafluoroethylene [TFE], 1180 g (18.4 mol) of vinylidene fluoride [VdF], and 2330 g (15.5 mol) of hexafluoropropylene [HFP] were charged thereto, and the temperature in the reactor was increased to 70° C. The pressure after the temperature increase was 3.88 MPa·G.

Subsequently, an aqueous solution in which 24 g of ammonium persulfate was dissolved in 50 g of water was press-charged into the reactor to initiate polymerization reaction. Since the pressure in the reactor decreased along with the progress of the polymerization reaction, a mixed gas of TFE/VdF/HFP (mixed molar ratio: 16.4/62.2/21.4) was charged to the reactor as divided charges to maintain the pressure in the reactor at 3.75 to 3.85 MPa·G. The addition of the divided charge gas was stopped when the total amount of divided charge gas was 10.2 kg (after about 10 hours), and aging was performed for about 30 to 50 minutes. The pressure in the reactor at this time was 1.8 MPa·G.

To 100 parts by weight of the obtained copolymer (copolymerization molar ratio of VdF/TFE/HFP/fluoroolefin iodide mixture=66.8/16.0/16.9/0.3), 20 parts by weight of MT carbon black, 5 parts by weight of zinc oxide, 5 parts by weight of triallyl isocyanurate (TAIC M60; a product of Nippon Kasei Chemical Co., Ltd.), and 3.5 parts by weight of organic peroxide (Perhexa 25B; a product of NOF Corporation) were added and kneaded. The resulting mixture was then subjected to press vulcanization at 180° C. for 10 minutes, followed by oven vulcanization at 230° C. for 22 hours. Thereafter, vulcanizate physical properties (according to JIS K6250 and K6253, which correspond to ASTM D412 and D2240, respectively), specific gravity, and compression set (according to ASTM D395 Method B) were measured.

The measurement results are shown in the following table.

TABLE

| Measurement item | | Ref. Ex. |
|---|---|---|
| Vulcanizate physical properties | | |
| 100% modulus | (MPa) | 4.6 |
| Elongation at break | (%) | 290 |
| Breaking strength | (MPa) | 24.1 |
| Compression set | | |
| 150° C., 70 hours | (%) | 20 |
| 200° C., 70 hours | (%) | 34 |
| 230° C., 70 hours | (%) | 61 |

The invention claimed is:

1. A mixture of fluoroolefin iodides represented by the general formulae:

$$C_nF_{2n+1}CF_2CH=CF(CF_2CF_2)_mI \quad [Ia]$$

$$C_nF_{2n+1}CF=CHCF_2(CF_2CF_2)_mI \quad [Ib],$$

wherein n is an integer of 0 to 5, and m is an integer of 1 to 3.

2. A method for producing a mixture of fluoroolefin iodides represented by the general formulae:

$$C_nF_{2n+1}CF_2CH=CF(CF_2CF_2)_mI \quad [Ia]$$

$$C_nF_{2n+1}CF=CHCF_2(CF_2CF_2)_mI \quad [Ib],$$

wherein n is an integer of 0 to 5, and m is an integer of 1 to 3, the method comprises subjecting a fluoroalkyl iodide represented by the general formula:

$$C_nF_{2n+1}CF_2CH_2CF_2(CF_2CF_2)_mI \quad [II],$$

wherein n is an integer of 0 to 5, and m is an integer of 1 to 3, to an HF-elimination reaction in the presence of a basic compound.

3. The method for producing a mixture of fluoroolefin iodides according to claim 2, wherein the basic compound is hydroxide, carbonate, or alkoxide of a monovalent or divalent metal.

4. The method for producing a mixture of fluoroolefin iodides according to claim 3, wherein the basic compound is used in the form of an organic solvent solution.

5. The method for producing a mixture of fluoroolefin iodides according to claim 4, wherein the basic compound is used in the form of an alcohol solution.

6. The method for producing a mixture of fluoroolefin iodides according to claim 5, wherein the alcohol solution containing the basic compound is used in a completely dehydrated state.

* * * * *